(12) United States Patent  
Duan et al.

(10) Patent No.: US 9,156,169 B2  
(45) Date of Patent: Oct. 13, 2015

(54) SYSTEM AND METHOD FOR ORIENTATION AND MOVEMENT OF REMOTE OBJECTS

(71) Applicants: Xiaodong Duan, Pleasanton, CA (US); Guohua Xiao, Plano, TX (US); Xinhong Wang, San Diego, CA (US)

(72) Inventors: Xiaodong Duan, Pleasanton, CA (US); Guohua Xiao, Plano, TX (US); Xinhong Wang, San Diego, CA (US)

(73) Assignee: ANKON TECHNOLOGIES CO., LTD., Wuhan, Hubei Province (CN)

( * ) Notice: Subject to any disclaimer, the term of this patent is extended or adjusted under 35 U.S.C. 154(b) by 0 days.

(21) Appl. No.: 14/275,893

(22) Filed: May 13, 2014

(65) Prior Publication Data

US 2014/0247039 A1    Sep. 4, 2014

Related U.S. Application Data

(63) Continuation of application No. 13/439,720, filed on Apr. 4, 2012.

(51) Int. Cl.
| | |
|---|---|
| *A61B 1/04* | (2006.01) |
| *A61B 5/06* | (2006.01) |
| *B25J 11/00* | (2006.01) |
| *A61B 1/00* | (2006.01) |
| *G01B 7/00* | (2006.01) |
| *G06T 7/60* | (2006.01) |
| *A61B 19/00* | (2006.01) |

(52) U.S. Cl.
CPC ............. *B25J 11/00* (2013.01); *A61B 1/00158* (2013.01); *A61B 1/041* (2013.01); *G01B 7/003* (2013.01); *G06T 7/602* (2013.01); *A61B 5/062* (2013.01); *A61B 2019/5251* (2013.01); *A61B 2562/162* (2013.01); *G06T 2207/10004* (2013.01)

(58) Field of Classification Search
CPC ................. A61B 1/041; A61B 5/6861; A61B 2562/162; A61B 5/061; A61B 5/062; A61B 5/06; A61B 5/07; A61B 5/073; A61B 5/4238; A61B 5/4255
USPC ............................ 128/899; 600/118; 335/219
See application file for complete search history.

(56) References Cited

U.S. PATENT DOCUMENTS

| | | | |
|---|---|---|---|
| 6,216,028 B1 | 4/2001 | Haynor et al. | |
| 7,341,063 B2 | 3/2008 | Garbibaldi et al. | |
| 7,523,756 B2 | 4/2009 | Minai et al. | |
| 7,540,288 B2 | 6/2009 | Viswanathan et al. | |
| 7,627,361 B2 | 12/2009 | Viswanathan | |
| 7,774,046 B2 | 8/2010 | Werp et al. | |
| 7,797,032 B2 | 9/2010 | Martinelli et al. | |
| 7,878,208 B2 | 2/2011 | Talman et al. | |
| 8,428,685 B2 | 4/2013 | Swain et al. | |
| 2004/0138555 A1 | 7/2004 | Krag | |
| 2004/0143183 A1 | 7/2004 | Toyoda et al. | |
| 2004/0199074 A1 | 10/2004 | Ritter | |
| 2005/0085720 A1 | 4/2005 | Jascob | |
| 2005/0139222 A1 | 6/2005 | Minai et al. | |
| 2005/0216231 A1* | 9/2005 | Aoki et al. ................... | 702/183 |
| 2007/0173691 A1* | 7/2007 | Yokoi et al. ................... | 600/118 |
| 2007/0295865 A1* | 12/2007 | Maini et al. ................... | 244/166 |

(Continued)

*Primary Examiner* — Charles A Marmor, II  
*Assistant Examiner* — Thaddeus Cox  
(74) *Attorney, Agent, or Firm* — Treasure IP Group, LLC

(57) ABSTRACT

The disclosed invention provides apparatus, systems, and methods for orientating an object in an enclosed area using a magnetic dipole deployed in the enclosed area and thereafter applying an external rotating magnetic field for applying a rotational force to the dipole along one or more selected axis. The external magnetic field is moved to manipulate object in the desired direction(s) of movement.

13 Claims, 13 Drawing Sheets

(56) References Cited

U.S. PATENT DOCUMENTS

| | | | |
|---|---|---|---|
| 2008/0161639 A1* | 7/2008 | Katayama et al. | 600/104 |
| 2008/0300458 A1* | 12/2008 | Kim et al. | 600/118 |
| 2009/0048484 A1* | 2/2009 | Swain et al. | 600/118 |
| 2009/0292174 A1* | 11/2009 | Shigemori | 600/117 |
| 2011/0046443 A1* | 2/2011 | Kawano et al. | 600/118 |
| 2013/0154776 A1* | 6/2013 | Mahoney et al. | 335/219 |
| 2013/0304446 A1* | 11/2013 | Rabinovitz et al. | 703/11 |

* cited by examiner

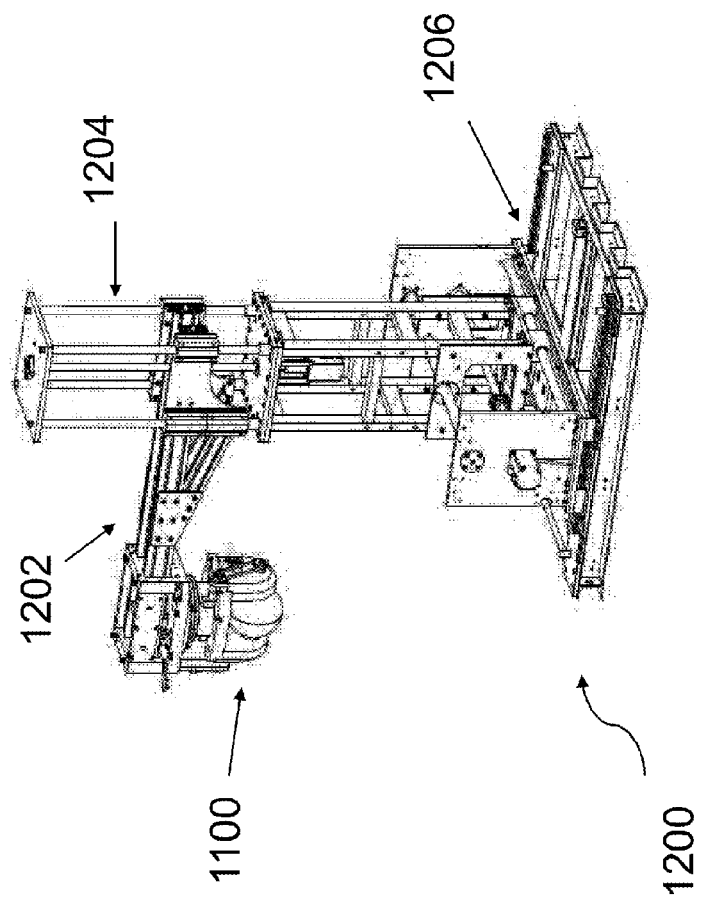

SYSTEM AND METHOD FOR ORIENTATION AND MOVEMENT OF REMOTE OBJECTS

TECHNICAL FIELD

The invention relates to the use of magnetic fields for the orientation and movement of remote objects. More particularly, the invention relates to systems and methods for orienting and moving a remote object having a magnetic field by using a rotatable magnetic field external to the object.

BACKGROUND OF THE INVENTION

The deployment of relatively small probes or sensors for performing tasks in confined, inaccessible, or remote spaces is useful in several contexts. For example, it is known in the arts to use wireless capsules for collecting images by equipping them with cameras, or for delivering doses of medication to general areas of the digestive system by equipping them with drug reservoirs. The currently available wireless capsules used in the medical field are carried by peristalsis through the digestive tract. In non-medical applications, a probe capsule may be carried by fluid flow and/or gravity through a system of piping or tubing. Such approaches utilize movement inherent in the environment being investigated, and the movement and orientation of the probes is left to chance to some extent. The challenges of providing controllable orientation and movement functions for remote probe technology are significant. Attempts to provide movement capabilities to remote probes have been made using mechanical drive systems. However, such systems require a significant amount of power, which is difficult to provide within the space available.

Due to the foregoing and possibly additional problems, improved apparatus, systems and methods for orientation and movement of remote objects would be useful contributions to the arts.

SUMMARY OF THE INVENTION

This application is related to U.S. application Ser. No. 12/753,931, which is incorporated herein in its entirety for all purposes by this reference. This application and the related application have one or more common inventors and are assigned to the same entity. In carrying out the principles of the present invention, in accordance with preferred embodiments, the invention provides controlled orientation and movement in remote objects. The embodiments described herein are intended to be exemplary and not exclusive. Variations in the practice of the invention are possible and preferred embodiments are illustrated and described for the purposes of clarifying the invention and are not intended to be restrictive. All possible variations within the scope of the invention cannot, and need not, be shown.

According to one aspect of the invention, in an example of a preferred embodiment, a method for moving an object in an enclosed area includes steps for placing an object comprising a magnetic dipole in the enclosed area and thereafter applying an external rotating magnetic field for applying a rotational force to the object along a variable axis. The external magnetic field is moved to manipulate object along the variable axis in the desired direction of movement.

According to another aspect of the invention, a system for moving an object in an enclosed area provides an object for placement in the enclosed area, the object having a magnetic dipole. The system also includes an external magnet configured for generating a rotating magnetic field for use in exerting a rotational force on the object. A control mechanism is provided for moving the external magnet in order to manipulate the object in the desired direction of movement.

According to an aspect of the invention, in preferred embodiments, methods and systems for orienting an object in an enclosed area include placing an object having a magnetic dipole in an enclosed area with a starting orientation. An external magnetic field is applied in proximity to the magnetic dipole and manipulated to interact with the magnetic dipole causing the object to adopt a second orientation relative to the starting orientation.

According to other aspects of the invention, in preferred embodiments, the remote object referred to herein is placed within a living medical patient, i.e., in vivo.

According to another aspect of the invention, a preferred method for moving an object in an enclosed area includes the step of placing an object comprising a magnetic dipole within the enclosed area. The object has support points where it can make contact with the surface of the enclosed area. In a further step, wherein one support point of the object is in contact with a surface of the enclosed area, an external rotating magnetic field is applied, causing the dipole to rotate. Thus changing the support point of the object in contact with the surface of the enclosed area, the external magnetic field is moved to manipulate the object in a desired direction of movement.

According to yet another aspect of the invention, in examples of preferred embodiments thereof, a system and method for observing an enclosed area provides for placing an object having a magnetic dipole and an image sensor in the enclosed area and applying an external rotating magnetic field. The external magnetic field is used to move the object for observing the area.

The invention has advantages including but not limited to providing one or more of the following features, orientation control for remote objects, controlled movement for remote objects, low power requirements for probe motion systems, and robustness of motion control elements. These and other advantages, features, and benefits of the invention can be understood by one of ordinary skill in the arts upon careful consideration of the detailed description of representative embodiments of the invention in connection with the accompanying drawings.

BRIEF DESCRIPTION OF THE DRAWINGS

The present invention will be more clearly understood from consideration of the description and drawings in which:

FIG. 13 is a diagram illustrating external magnet moving apparatus and systems according to preferred embodiments of the invention.

References in the detailed description correspond to like references in the various drawings unless otherwise noted. Descriptive and directional terms used in the written description such as up, down, horizontal, vertical, upper, side, et cetera; refer to the drawings themselves as laid out on the paper and not to physical limitations of the invention unless specifically noted. The drawings are not to scale, and some features of embodiments shown and discussed are simplified or amplified for illustrating principles and features as well as advantages of the invention.

DESCRIPTION OF PREFERRED EMBODIMENTS

While the making and using of various exemplary embodiments of the invention are discussed herein, it should be appreciated that the apparatus and techniques for its use exemplify inventive concepts which can be embodied in a wide variety of specific contexts. It should be understood that the invention may be practiced in various applications and embodiments without altering the principles of the invention. For purposes of clarity, detailed descriptions of functions, components, and systems familiar to those skilled in the applicable arts are not included. In general, the invention provides apparatus, systems, and methods for moving and orienting remote objects. The invention is described in the context of representative example embodiments. Although variations and alternatives for the details of the embodiments are possible, each has one or more advantages over the prior art.

Figure 1:
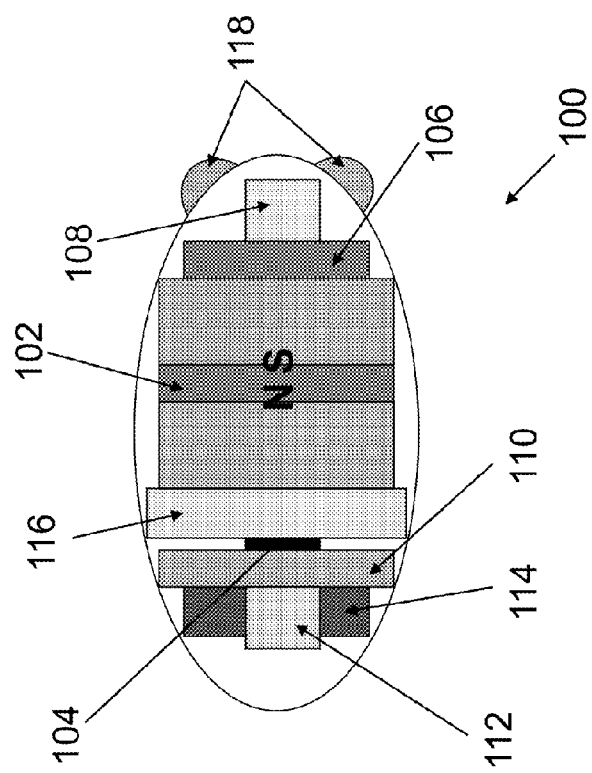
FIG. 1 is a simplified partial cutaway view of an example of apparatus according to preferred embodiments of the invention.
Figure 2:
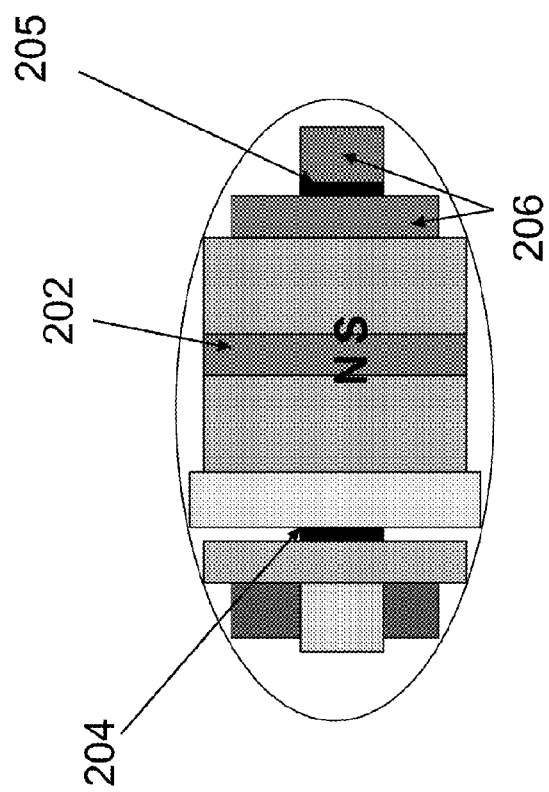
FIG. 2 is a simplified partial cutaway view of an alternative example of apparatus according to preferred embodiments of the invention.

Referring primarily to FIG. 1, in an example of a preferred embodiment, an endoscope capsule apparatus 100 is shown. The principles of the invention shown and described may also be applied to additional uses in vivo or to probes used in other contexts such as mechanical or fluid-handling systems. The term "capsule" is used interchangeably with the term "probe" herein to refer to probe apparatus and similar remote objects in general, regardless of shape. It should be understood that a capsule may be spherical, cylindrical, substantially cylindrical with hemi-spherical ends, or other suitable shapes or combinations of shapes. The capsule 100 includes a magnetic dipole 102. In this example the magnetic dipole's 102 axis is aligned with the capsule's 100 axis. A magnetic field sensor 104 is included. A pair of magnetic sensors may also be used. The magnetic field sensor(s) 104 is (are) aligned with the dipole 102 in order to sense the x-, y-, and z-axis magnetic field. In this example, the z direction is along the capsule axis. The magnetic field values sensed with the magnetic field sensor 104 are preferably sent out from the capsule 100 using an included RF transmitter 106 and antenna 108. As shown in this example, an image sensor 110, lens 112, and one or more LEDs 114 may be included in the capsule 100 for medical imaging purposes, along with associated processing circuitry 116 for processing, storing, and/or sending image data. Friction force may be used to stabilize the capsule 100 during orienting and/or moving maneuvers, thus it is preferred to increase the static friction force at selected points such as near the ends of the capsule by modifying the materials and/or texture and/or shape of the capsule accordingly. Preferably, "feet" 118 are included on the external surface of the capsule 100 in locations selected for enhancing friction. The feet preferably take the form of rings, ridges, protrusions, or roughened surfaces. This is one example of a particular implementation possible within the scope of the invention. The principles of the invention are not limited to this particular implementation and many variations are possible. Another example of an endoscope capsule is shown in FIG. 2. A magnetic dipole 202 is included with one or a pair of magnetic field sensors 204. The magnetic dipole's axis is preferably aligned with the capsule's axis (z). The magnetic field sensors 204 are aligned with the dipole 202 for sensing the x-, y-, and z-axis of the magnetic field. A three-dimension gravity sensor 205 is also preferably included. As in the above example, the measured magnetic field values and sensor data may be sent to an external receiver (not shown) using an RF link 206. It should be appreciated that many other variations in the details and arrangement of components may be made within the scope the invention.

With the overview of the exemplary apparatus of FIGS. 1 and 2 in mind, it should be understood that the determination of the position of the of a capsule in a stationary state with one three-dimension magnetic sensor is shown by:

$$B^m{}_{sensor}(r_x,t) = R(\alpha,\beta,\gamma)B^m{}_{magnet\_ball}(r_x-r_0) + B^m{}_{capsule\_dipole}(r_s) + B_{earth}$$

$$B_{magnet\_ball}(r_s-r_0) = R(\alpha,\beta,\gamma)B^m{}_{magnet\_ball}(r_x-r_0)$$

Wherein, B is the magnetic field, R is the rotation function linking the locally sensed magnetic field to an externally applied magnetic field provided by an external magnet as further described herein. The earth's magnetic field, $B_{earth}$, is small (about 0.2 to 0.4 Gauss) and generally can be neglected.

$$B^m{}_{capsule\_dipole}(r_{s \to i})$$

is fixed and can be pre-measured, at about 100 Gauss, for example.

$$B_{magnet\_ball}(r_s-r_0)$$

can be modeled as the dipole magnetic field (in the range of about 10~300 Gauss). The $r_0$ is the original magnetic ball location and orientation, thus at one external magnet position, three descriptive equations are available. When two magnetic field sensors are used in the capsule, as shown in FIG. 2, the step of shifting the external magnetic field may be omitted, since the two magnetic field sensors provide sufficient data to make the calculations.

Figure 3:
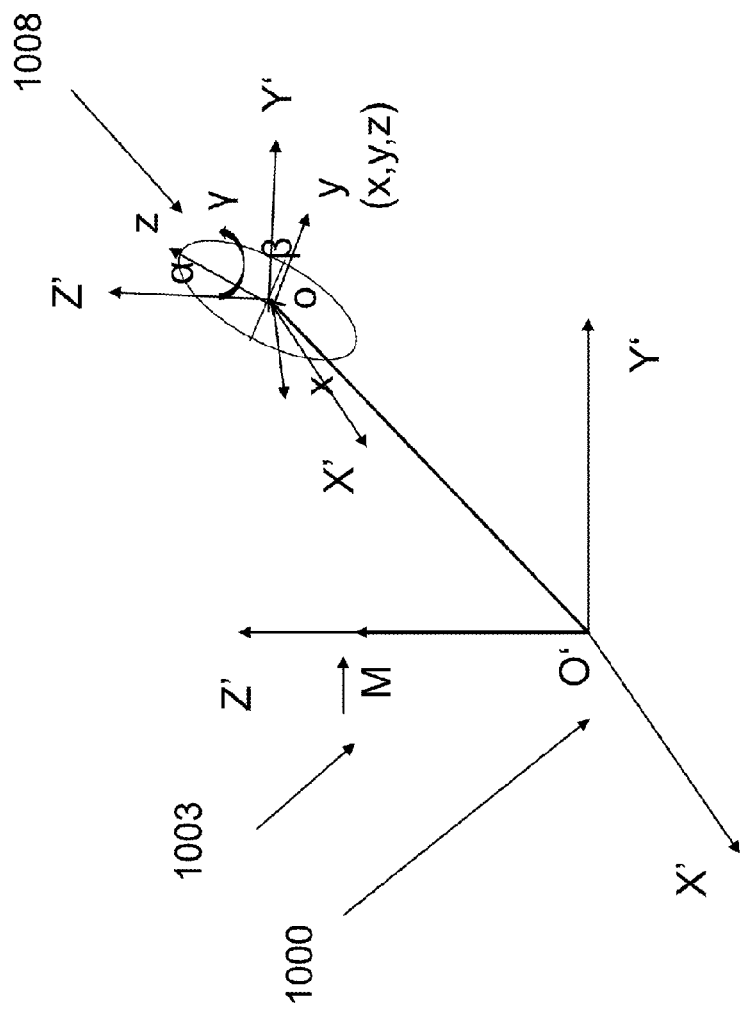
FIG. 3 is a conceptual diagram illustrating an overview of the operation of apparatus, systems and methods of the invention.
Figure 4:
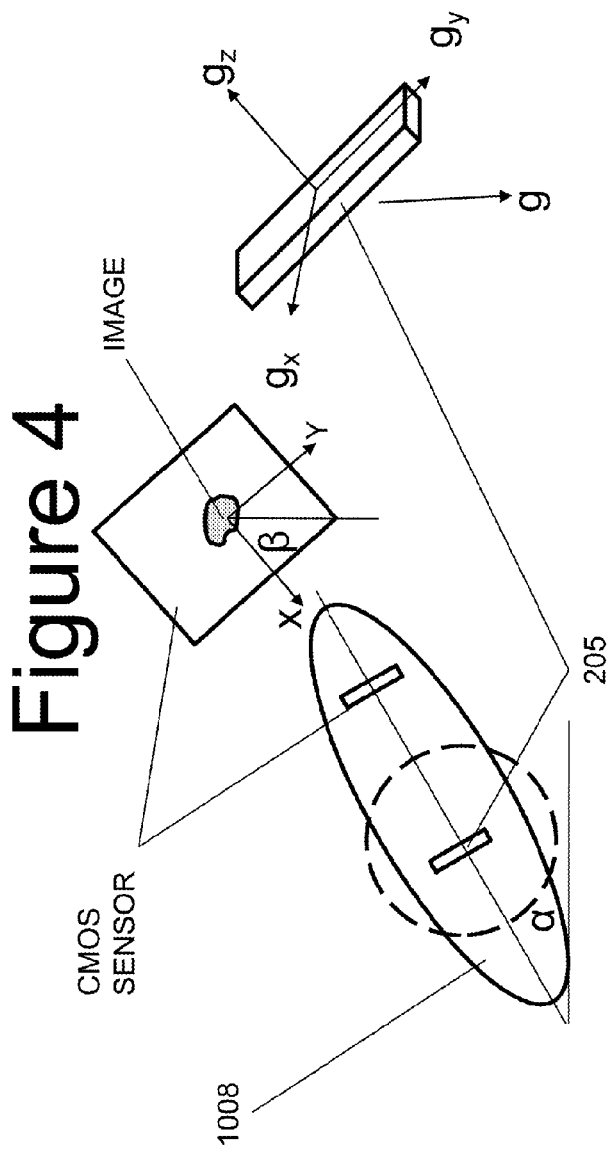
FIG. 4 is a conceptual diagram illustrating an overview of the operation of apparatus, systems and methods of the invention.

FIG. 3 shows a conceptual view of an example of the coordination among the various forces. A substantially spherical magnetic ball (not shown) has a magnetic field, represented by arrow 1003, which has the magnetic moment of M, which forms the dipole magnetic field, the magnet is located at the X', Y', Z' coordinate's (1000) point of origin O'. The capsule 1008 is in the field of the magnetic ball 1003. Assuming that the capsule 1008 remains at one location in a stationary state, shifting the external magnet, and thus the magnetic field 1003, between two different positions thus provides a total six equations, so that x, y, z, α, β, and γ, can be reverse-calculated as the capsule 1008 location and angles. Additionally referring to FIG. 4, the use of the three-dimension gravity sensor for aligning the capsule and its imaging apparatus, such as an on-board CMOS imaging sensor is illustrated. The three-dimension gravity sensor 205, with gravity readings of $g_x$, $g_y$, and $g_z$ from the x, y, and z axis respectively, is used to determine the angle α of the capsule 1008 relative to horizontal plane, or the Earth. When the position of the capsule 1008 is static, the α can be calculated:

$$\cos\alpha = \frac{g_z}{\sqrt{g_x^2 + g_y^2 + g_z^2}}$$

Preferably, for imaging purposes, the CMOS sensor is mounted in a parallel relationship with the gravity sensor 205. Assuming that the X direction of the CMOS sensor is the same as the x axis of the gravity sensor, and further assuming that the Y direction of CMOS image sensor is the same as y axis of gravity sensor, the rotation angle β of the CMOS sensor, or a captured image therefrom, can be calculated from the readings of $g_x$ and $g_y$:

$$tg\beta = \frac{g_y}{g_x}$$

Again referring primarily to the overview of the exemplary apparatus of FIG. 2, the force and torque on the capsule for the two magnetic sensor structure may be calculated from the values given by the two magnetic field sensors as follows.

$$T = m \times (B_m - B_{dipole}), F = m \cdot (B_m - B_{dipole})$$

Wherein, m is the magnetic moment of the dipole. The gradient of the magnetic field can be calculated by the difference between the measurements taken by the two magnetic field sensors.

$$(B_m - B_{dipole}) \begin{vmatrix} \frac{B_{m1x} - B_{d1x} -}{B_{m2x} - B_{d2y}} & \frac{B_{m1y} - B_{d1y} -}{B_{m2y} - B_{d2y}} & \frac{B_{m1z} - B_{m2z} -}{B_{m2z} - B_{d2z}} \\ \frac{x_1 - x_2}{B_{m1x} - B_{d1x} -} & \frac{x_1 - x_2}{B_{m1y} - B_{d1y} -} & \frac{x_1 - x_2}{B_{m1z} - B_{d1z} -} \\ \frac{B_{m2x} - B_{d2y}}{y_1 - y_2} & \frac{B_{m2y} - B_{d2y}}{y_1 - y_2} & \frac{B_{m2z} - B_{d2x}}{y_1 - y_2} \\ \frac{B_{m1x} - B_{d1x} -}{B_{m2x} - B_{d2y}} & \frac{B_{m1y} - B_{d1y} -}{B_{m2y} - B_{d2y}} & \frac{B_{m1z} - B_{d1z} -}{B_{m2z} - B_{d2x}} \\ \frac{z_1 - z_2}{} & \frac{z_1 - z_2}{} & \frac{z_1 - z_2}{} \end{vmatrix}$$

The force and torque are preferably calculated in real time during movement, monitoring the magnetic force in order that the capsule can be prevented from overshooting the desired position.

In general, aligning and orienting an object deployed in a remote environment is accomplished by applying an external magnetic field to interact with the object's dipole such that the object is caused to rotate, move axially, or both. Thus, there is no requirement to carry a power source such as a battery within the object, such as a remote probe or capsule, in order to power movement. The external magnetic field is preferably rotatable through 360 degrees. Using the magnetic sensor(s) in the capsule, the largest magnetic field is found during the rotation of the external magnet. Since the magnetic dipole in the capsule has a tendency to turn along the magnetic field, the largest magnetic field value is used to indentify when the dipole in the capsule is in alignment with the axis of the external magnet. The dipole magnetic field is described by;

$$B_z^m = \frac{\mu_0}{4\pi} \frac{M}{D^3} + B_z^{dipole}$$

Figure 5:
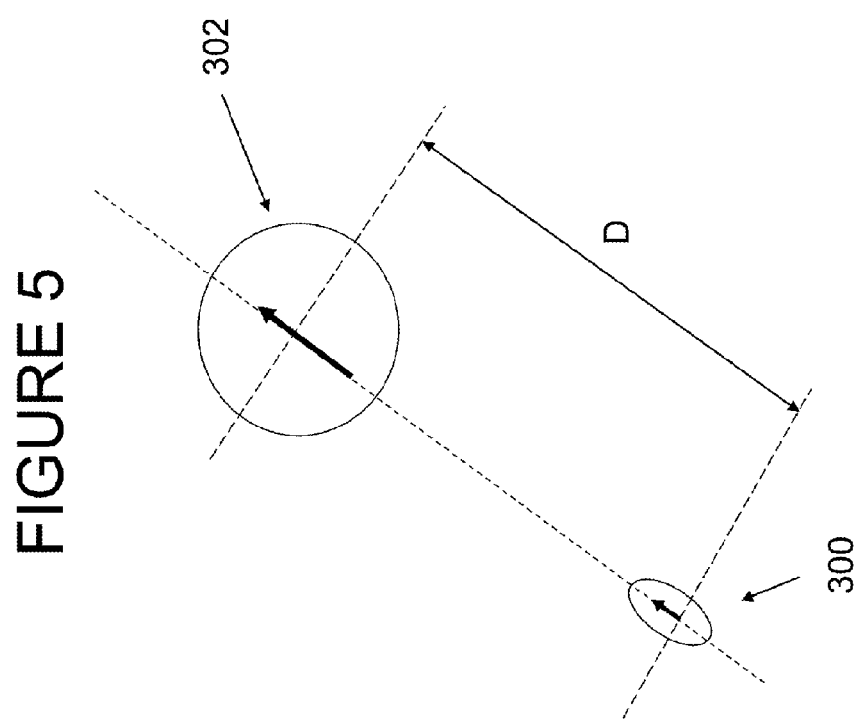
FIG. 5 is a conceptual diagram illustrating the operation of apparatus, systems and methods of the invention.

Wherein, M is the magnetic moment of the external magnet, which is in control of the user and is known. $B_z^m$ is the measured magnetic field. $B_z^{dipole}$ is the measured magnetic field of the capsule in the absence of the external magnet. The distance D is calculated from the above equation, thus the location and orientation of the capsule can be determined. This relationship is also shown in FIG. 5.

The magnetic forces between the external magnet and magnetic dipole inside the capsule reduces quickly with distance. It should be appreciated that for medical implementations, the dipole magnet is necessarily small relative to the dimensions of the human body. In some applications, the use of larger dipole magnets may be preferable. The forces generated by the magnetic field may be separated into two types; magnetic field gradient force, and magnetic field torque force. For the approximation of the external magnet and magnetic dipole inside the capsule, the forces are shown by;

$$f_g = \frac{\mu_0}{4\pi} \frac{6Mm}{D^4}$$

$$f_t = \frac{\mu_0}{4\pi} \frac{2Mm}{D^3 r}$$

Wherein $f_g$ is the magnetic field gradient force, and $f_t$ is the magnetic field torque force. M is the magnetic moment of the external magnet and m is the magnetic moment of the capsule dipole. D is the distance from the external magnet to the magnetic dipole of the capsule, center to center. The length of the capsule dipole is represented by r. Comparison of the two forces reveals that as the distance D increases, the magnetic field torque force dominates.

$$\frac{f_t}{f_g} = \frac{D}{3r}$$

Figure 6:
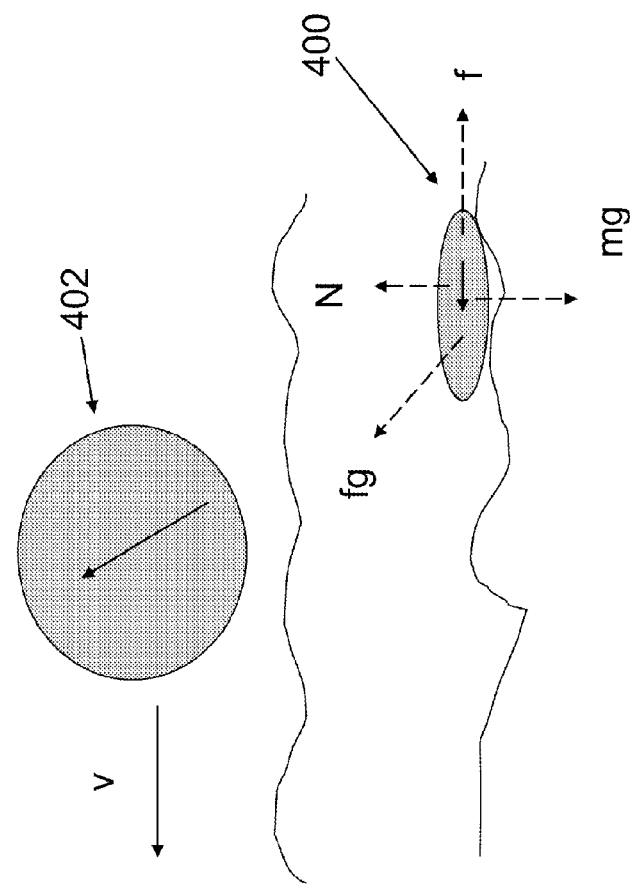
FIG. 6 is a conceptual diagram illustrating the operation of apparatus, systems and methods of the invention in an exemplary operating environment.
Figure 7:
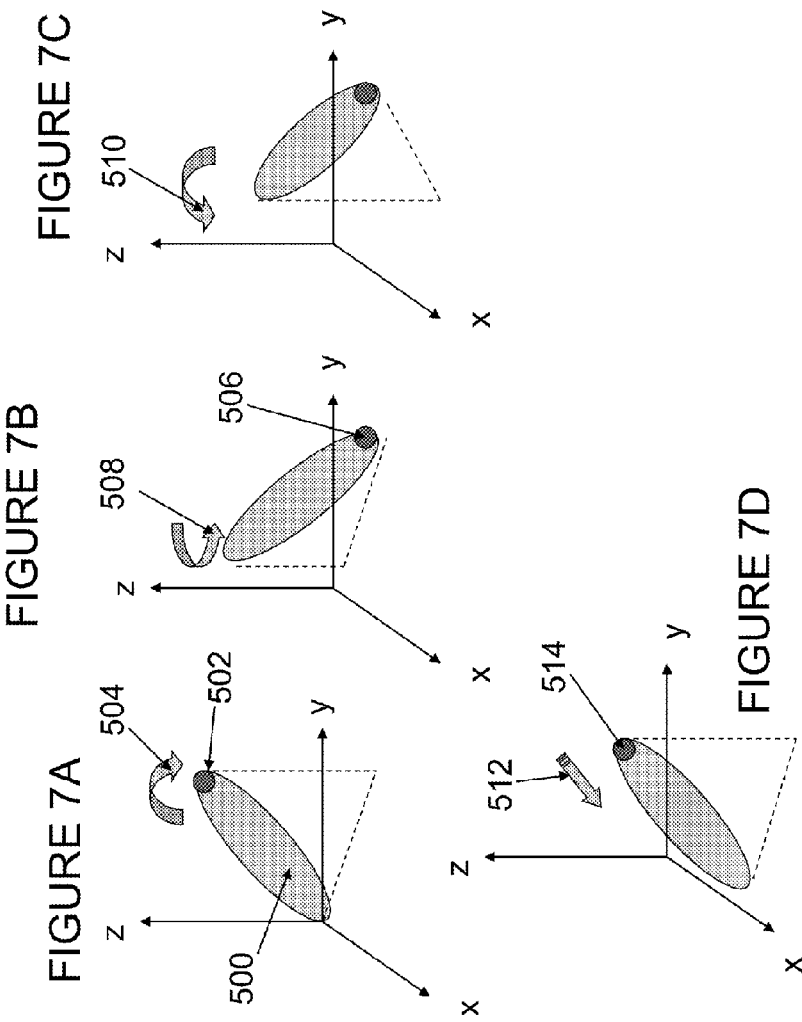
FIGS. 7A-7D are a series of conceptual diagrams portraying an example of a preferred alternative embodiment of a system and method steps of the invention.

It has been found that there are several factors that may make directly dragging, or pushing, the capsule with an external magnet difficult to control. The magnetic field gradient force may not be exactly along the desired direction of movement. Obstacles, such as surface irregularities may lie in the desired path of movement. The magnetic field gradient force must overcome the forces of friction between the capsule and the surfaces it comes into contact with. Variations in static friction and dynamic friction may cause the capsule to alternately stick and slip, making movement erratic. The relationship between the various forces and how they interact is shown in the simplified diagram of FIG. 6. The external magnet 402 is shown being used in an effort to drag a capsule 400 in an operating environment, such as through a passage in vivo for example. Preferably, a robot is used to control the movement of the external magnet 402. The magnetic field of the external magnet forms a link with the magnetic field of the capsule dipole, indicated by the gradient force $f_g$. As can be seen, the path of movement, axis of the capsule, and the direction of the gradient force cannot be precisely aligned. Friction f impedes movement, and potential obstacles lie ahead. According to preferred embodiments of the invention, the capsule may be "walked", overcoming some of the impeding forces. This enhanced method of movement is accomplished by altering support points and applying rotational force. For the purposes of this description "support points" refers to selected points at which the surface of the capsule may make contact with the surface on which it is deployed. It has been found that causing the capsule to reorient among its support points can be used to advantage in facilitating movement. For example, now referring primarily to FIGS. 7A through 7D, it can be seen that by shifting the support points and reorienting the capsule, the capsule can move along x. In FIG. 7A, a capsule 500 is shown in a starting orientation. A support point at the surface of the capsule 500 is shown at 502. A rotational force, indicated by arrow 504, is applied by the interaction of the external magnetic field with the capsule dipole, causing the support point to move to 506. In FIG. 7B, the starting orientation is with the support point at 506. A rotational force 508 is again applied, and again at 510 (FIG. 7C), and as the external magnet is moved laterally, the capsule also moves laterally in the direction of arrow 512 in FIG. 7D, adopting a new support point indicated by 514. By rotating the external magnetic field, the magnetic link between the external magnetic field and the capsule dipole is used to overcome the torque of the capsule's weight. Thus the force of friction need not be overcome as necessary in merely dragging the capsule. The method in fact uses the force of friction to advantage to the extent that it allows the capsule to be "walked" forward. This approach to movement of the capsule has been found to be more effective in many cases than dragging, magnetically levitating, or pushing alone. As the angle between the axis of the capsule and the direction of movement can be changed at the different steps, the capsule walking direction can be changed.

Figure 8:
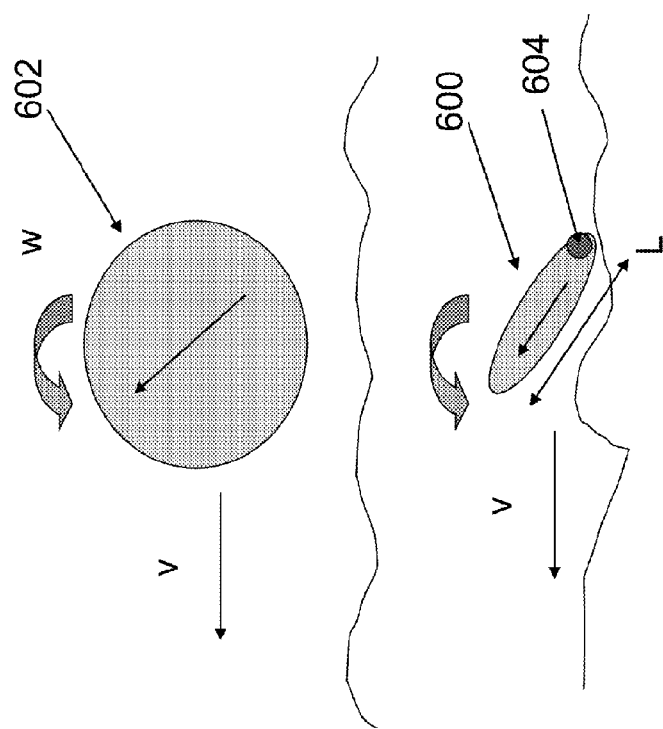
FIG. 8 is a conceptual diagram illustrating a preferred alternative embodiment of systems and method steps of the invention.
Figure 9:
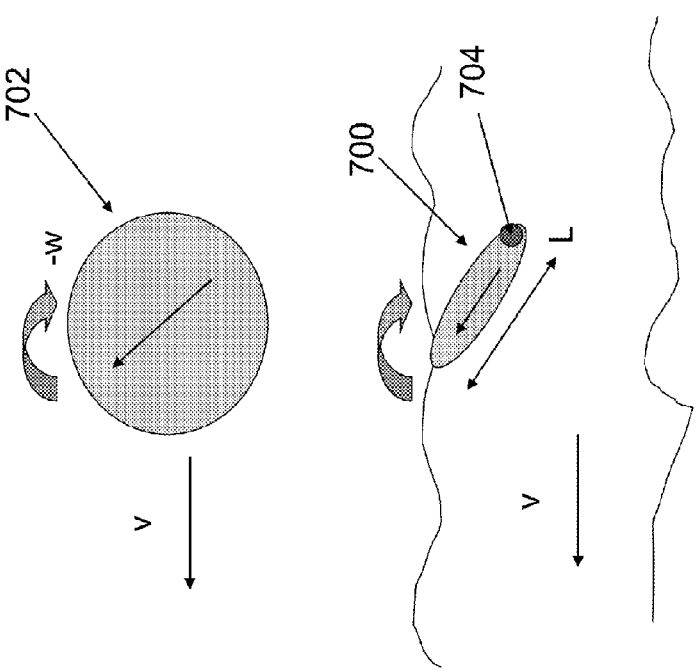
FIG. 9 is another conceptual diagram illustrating a preferred alternative embodiment of systems and method steps of the invention.

An example of a special case of capsule movement using these principles is illustrated in FIG. 8. In this example, the capsule 600 is more-or-less somersaulted along a movement path (indicated by arrow v). The external magnet 602 is rotated and moved laterally along the movement path v. The resultant magnetic forces exerted between the external magnet and the capsule dipole cause the support point 604 to alternate end-over-end as the capsule 600 moves along the movement path v. Note that the external magnet is rotated in the same direction as its lateral motion. It has been found that in order to make the best forward movement, the relation of the moving speed v and rotating speed w should be v=wL for the external magnet, wherein L is the length of the capsule. In environments where the surface to be moved over is not smooth, this or a variation of this method of movement is advantageous for overcoming obstacles. In another example of a movement technique, when the distance between external control magnet(s) and the capsule is not too great, the capsule can be magnetically levitated. Magnetic levitation refers to the overcoming of the force of gravity for other than horizontal movement. As in "walking" the capsule as described herein, the static friction force between the capsule and the "wall" of the operating environment, such as an intestine or stomach for in vivo implementations, may be used to stabilize the capsule and to advance its movement in any direction. The alternating supporting points "walking" technique may also be applied in such maneuvers, in effect causing the capsule to climb a vertical or sloped surface, or for causing the capsule to travel along an inverted surface. In the example shown in FIG. 9, the capsule is rotated along an inverted surface and is simultaneously moved forward laterally by the manipulation of the external magnet. Note that the external magnet is rotated in the direction opposite to its lateral motion. Similar to the previous case, it has been found that a moving speed of v=−wL is preferable (w being negative to indicate the reverse rotation).

Figure 10:
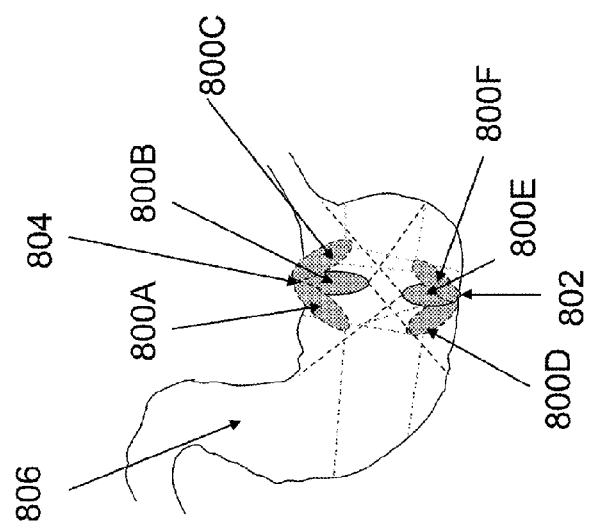
FIG. 10 is a conceptual diagram illustrating a preferred alternative embodiment of systems and method steps of the invention in an exemplary operating environment.
Figure 11:
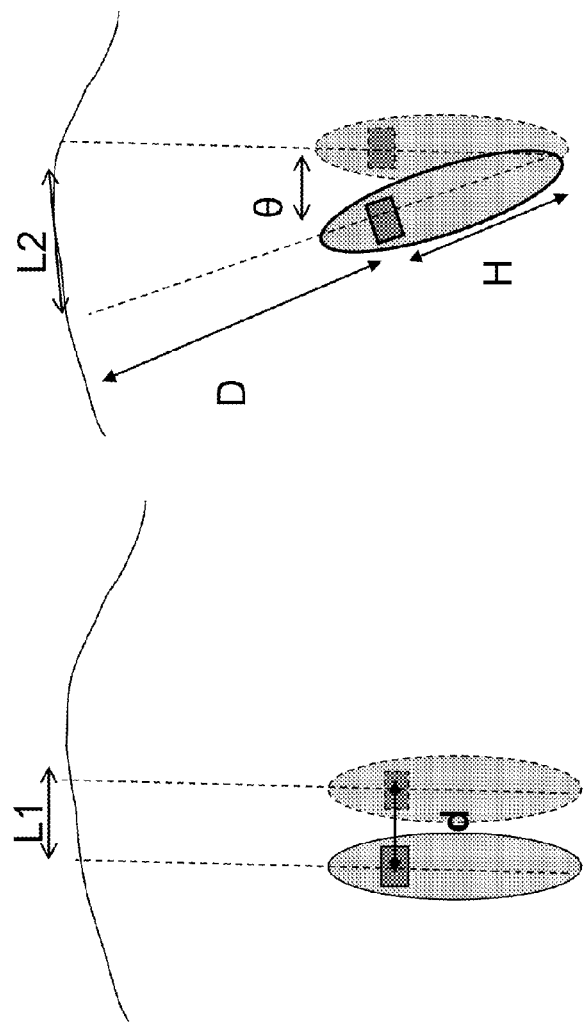
FIG. 11 is another conceptual diagram illustrating a preferred alternative embodiment of systems and method steps of the invention in an exemplary operating environment.

FIGS. 10 and 11 are illustrative of the apparatus, systems and methods of orienting and moving a capsule equipped with an image sensor in vivo. In FIG. 10, a conceptual view shows that by relocating the capsule 800 to relatively few vantage points 802, 804, within an operating environment, e.g., the stomach, and by reorienting (shown by 800A-F) the capsule 800 while positioned at these vantage points 802, 804, nearly the entire surface of the stomach 806 can be observed. Of course, deploying the capsule at additional locations facilitates observing the entire operating environment, or in some cases, may be used for observing one selected target location from multiple viewing angles. It should be appreciated by those skilled in the arts that location and/or imaging data or other data obtained from a remote sensor using the orientation and movement apparatus and methods described herein may use the data gathered by the probe to provide feedback for orientation and/or motion control, preferably in real time. FIG. 11 illustrates an alternative method of combined imaging and navigation, in a preferred embodiment wherein image analysis may be used not only for guiding capsule navigation, but in a method for determining distances and volumes from image analysis using a magnetically controlled remote probe system. As shown, at a point A, the capsule may be shifted a distance d, and images obtained by an on-board image sensor are also shifted relative to each other as shown at L1. Assuming that a corresponding pixel is defined by length p, the pixel p=d/L1. At the same point, using the rotating magnetic field to reorient the capsule in two different but closely spaced positions, and taking an image at each position, the images are shifted from each other by L2, in terms of the pixels. Thus the distance from the image sensor to the imaged surface is:

$$D = \frac{pL2}{\theta} - H$$

Wherein θ is the angle between the first orientation and the second orientation, and H is the distance from the image sensor to the end of the capsule farthest from the surface. Reiterating these steps, the spatial dimensions of the target environment can be determined. Alternatively, the images thus obtained, pixel by pixel, may be combined using stereoscopic imaging techniques and equipment in order to render 3D images of the targeted area.

Figure 12:
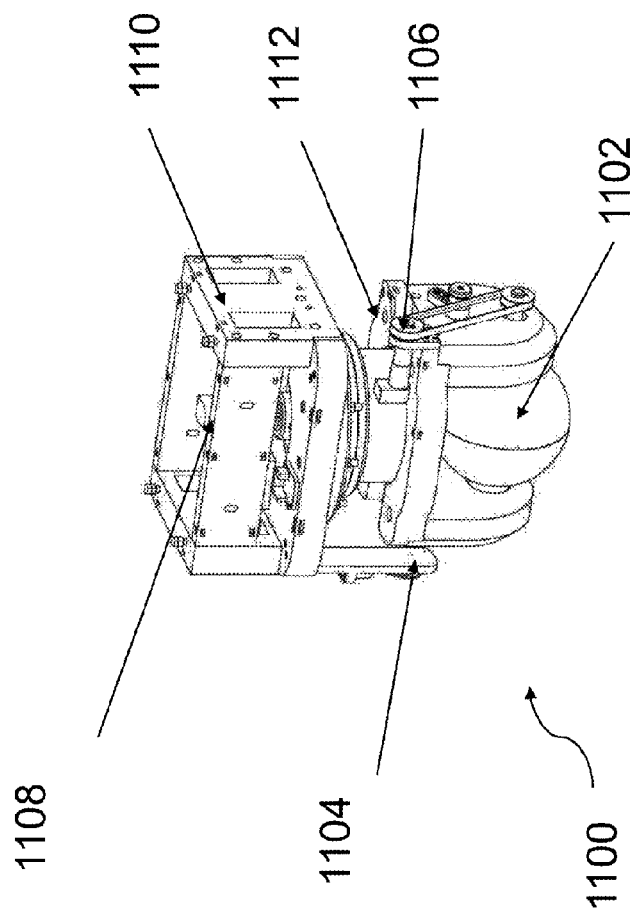
FIG. 12 is a close-up diagram illustrating a portion of magnet moving apparatus and systems according to preferred embodiments of the invention.

FIGS. 12 and 13 depict apparatus 1100 for moving external magnets relative to a capsule in accordance with the invention as described herein. As shown, a magnet 1102, preferably approximately spherical, is secured in a rotation frame 1104. The magnetic pole of the magnet 1102 is preferably in alignment with the intended orientation for vertical rotation. A vertical rotation servo motor 1106 is preferably provided, as is a horizontal rotation servo motor 1108, each of which is supported by a suitable frame, 1110, 1112, respectively. The supporting frames, e.g. 1110, 1112, are made from non-ferromagnetic material such as plastics or selected metals such as aluminum, copper, or selected alloys. The servo motors 1106, 1108, are preferably equipped with non-magnetic position sensors (not shown), such as laser or other optical sensors configured to provide guidance for controlling the movement of the motors. The vertical rotation motor 1106 is designed to impart rotation to the magnetic ball 1102. The horizontal rotation motor 1108 provides rotation in the horizontal plane. As shown in FIG. 13, the apparatus 1100 preferably also includes fixtures adapted for horizontal and vertical positioning of the magnetic ball 1102 by the use of vertically and horizontally adjustable mechanisms, e.g., 1202, 1204 and an adjustable base 1206. It can be seen that providing the external magnet with freedom of movement along two axes facilitates the practice of the techniques described herein for tracking and moving in the X, Y, and Z directions. The preferred embodiment shown is exemplary, and alternative structures may be used without departing from the invention so long as sufficient freedom of movement is provided.

Capsules used for medical implementations may be equipped with one or more of the following: medical diagnostic tools, medical therapy tools, or surgical tools. Medical diagnostic tools are devices that aid in the examination of the bodily conditions of the area in which the capsule is deployed. These tools can include sensors that take images or measure the temperature, pressure, PH, and the like. In some versions of the invention, medical diagnostic tools may also include devices that collect physical samples from the area and deliver the samples outside of the body for further testing. Medical therapy tools refer to treatment devices meant to treat an existing medical condition. For example, these tools may include drug delivery units, medical light sources for photodynamic therapy, or controlled heat sources for hypothermia therapy. Medical surgical tools include devices that can perform surgical operations in vivo.

The apparatus, systems and methods of the invention provide one or more advantages including but not limited to one or more of, improved remote object orientation and motion control, reduced remote probe power requirements. While the invention has been described with reference to certain illustrative embodiments, those described herein are not intended to be construed in a limiting sense. For example, variations or combinations of features or materials in the embodiments shown and described may be used in particular cases without departure from the invention. Although the presently preferred embodiments are described herein in terms of particular examples, modifications and combinations of the illustrative embodiments as well as other advantages and embodiments of the invention will be apparent to persons skilled in the arts upon reference to the drawings, description, and claims.

We claim:

1. A method for moving and orienting an object in an enclosed area comprising the steps of:
    1) providing an object comprising a magnetic dipole, and first and second support points, wherein the support points comprise high friction substances, positioned at ends of the object, and do not wrap around a perimeter of the object; and wherein magnetization directions of the magnetic dipole are parallel to a length of the object;
    2) providing an external magnet configured for generating an all-direction rotatable and movable magnetic field in proximity to the magnetic dipole, generating an external magnetic field for the object, and manipulating the external magnetic field to interact with the magnetic dipole, wherein the external magnet is disposed in a system comprising vertically and horizontally adjustable mechanisms and an adjustable base, adapted to control the vertical and horizontal positions of the external magnet; and
    vertical and horizontal rotation servo motors to impart rotation of the external magnet, and each rotation servo motor is equipped with a respective sensor to provide guidance for controlling the movement of the rotation servo motor thereof;
    3) using the vertically and horizontally adjustable mechanisms and controlling the adjustable base to place the object comprising a magnetic dipole in the enclosed area, wherein the object adopts a first orientation according to a direction of the magnetic field;
    4) adjusting the vertical servo motor to impart a first rotation of the external magnet to orient the object to adopt a first orientation in response to a rotation of the external magnet, wherein the object is in contact with a first part of a surface of the enclosed area through the first support point; adjusting the horizontal rotation servo motor to control the external magnetic to change a movement direction of the object while being supported by the first support point;
    5) adjusting the vertical servo motor to impart a second rotation of the external magnet to flip the object to adopt a second orientation by applying a rotational magnetic field through the external magnet, wherein the object is in contact with a second part of the surface of the enclosed area through the second support point; adjusting the horizontal rotation servo motor to control the external magnetic to change another movement direction of the object while being supported by the second support point;
    6) adjusting the vertical servo motor to impart a third rotation of the external magnet to flip the object to adopt a third orientation, wherein the object is in contact with a third part of the surface of the enclosed area through the first support point again, wherein the third orientation is a translation of the first orientation; and
    7) steps 3)-6) are repeated to precisely place the object to a target location at a target orientation.

2. The method according to claim 1, wherein the step of placing an object in an enclosed area further comprises placing the object in vivo.

3. The method according to claim 1, comprising the further steps of:
    capturing an image at the first orientation;
    capturing a separate image at another orientation; and
    using the captured images to calculate the spatial dimensions of the area.

4. The method according to claim 1, wherein the object performs a rotation at the second orientation.

5. The method according to claim 1, wherein the object carries a power supply.

6. The method according to claim 1, wherein the object does not carry an electrical power supply.

7. The method according to claim 1, wherein the magnetic field can move 360 degrees.

8. The method according to claim 1, further comprising determining a position and orientation of the object by deriving a distance D from a known magnetic moment M of the external magnet.

9. The method according to claim 1, further comprising determining a position and orientation of the object by deriving a distance D from a measured magnetic field $B_z^m$.

10. The method according to claim 1, further comprising determining a position and orientation of the object by deriving a distance D from a measured magnetic field $B_z^{dipole}$ in the absence of the external magnet, wherein distance D is a distance between a center of the magnetic dipole in the object and a center of the external magnet.

11. The method according to claim 1, wherein the object adopts another orientation by a magnetic field gradient force.

12. The method according to claim 1, wherein the object adopts another orientation by a magnetic field torque force.

13. The method according to claim 12, wherein an axis of the object and a direction of the gradient force cannot be precisely aligned.

\* \* \* \* \*